US00PP27983P2

(12) United States Plant Patent
Doyle

(10) Patent No.: US PP27,983 P2
(45) Date of Patent: May 9, 2017

(54) FIG TREE NAMED 'S-64'

(50) Latin Name: *Ficus carica*
Varietal Denomination: S-64

(71) Applicant: James F. Doyle, Roseville, CA (US)

(72) Inventor: James F. Doyle, Roseville, CA (US)

(73) Assignee: James F. Doyle, Roseville, CA (US)

( * ) Notice: Subject to any disclaimer, the term of this patent is extended or adjusted under 35 U.S.C. 154(b) by 39 days.

(21) Appl. No.: 14/756,893

(22) Filed: Oct. 26, 2015

(51) Int. Cl.
*A01H 5/08* (2006.01)

(52) U.S. Cl.
USPC ..... Plt./211

(58) Field of Classification Search
USPC ..... Plt./211
See application file for complete search history.

*Primary Examiner* — Keith Robinson
(74) *Attorney, Agent, or Firm* — Randall Danskin P.S.

(57) ABSTRACT

A new and distinct variety of fig tree is disclosed, and which produces a green to yellow skinned fig fruit of the common, or persistent type, and which further has an excellent size, and which additionally holds its size later in the season than other commercial fig varieties under the ecological conditions prevailing in the San Joaquin Valley of central California.

3 Drawing Sheets

Latin name: *Ficus carica.*
Varietal denomination: 'S-64'.

BACKGROUND OF THE NEW VARIETY

The present invention relates to a new, novel and distinct variety of fig tree, and which has been denominated varietally as 'S-64', and more specifically to a novel fig tree which produces green to yellow skinned figs of the common, or persistent type, and wherein the fruit has an excellent size and holds up its size later into the growing season than many other known commercial fig varieties thus extending the season for prime-sized and quality fresh figs when the new fig tree is grown under the ecological conditions prevailing in the San Joaquin Valley of central California.

ORIGIN AND ASEXUAL REPRODUCTION OF THE NEW VARIETY

It has long been recognized that many important factors contribute to the success of any new variety of fig, and especially figs for the fresh market. For example, one important factor is the relative date of harvesting of the new variety in comparison to other similar varieties bearing similar fruit in the same season. Further, another significant factor affecting the commercial viability of any variety of new fruit, such as figs, relates to its appearance as well as its fruit size, and an exceptional flavor.

The new fig tree variety 'S-64', as disclosed, hereinafter, was derived by the methodology which is set forth, as follows. The inventor developed the present, new variety of fig tree 'S-64' as a result of a controlled, hybrid cross-pollination which was made in the summer of 2010. The aforementioned cross-pollination involved the fig tree variety 'Desert King' [unpatented], which was used as the seed [female] parent; and the caprifig tree '91C' [unpatented], and which was used as the pollen [male] parent. The caprifig tree '91C' is a proprietary tree which was developed, and is owned by the Inventor. In this regard, the pedigree of the caprifig tree '91C' includes genes from both the 'CA Brown Turkey' fig tree variety [unpatented], and the 'Calimyrna' fig tree variety [unpatented], both of which are widely grown in the state of California.

The fruit produced by the 'Desert King' fig tree was first covered with a cloth cage prior to the time of pollen receptivity. This cloth cage protected the fruit during the growing seasons so that insects that might cause unwanted pollination would be excluded. During the manual pollination process, the cloth cage was subsequently removed, and then replaced immediately after the manual pollination, until such time as the fruit attained full maturity.

After the aforementioned hybridized fruit attained maturity in the fall of 2010, about 500 seeds were harvested from this aforementioned fruit, and were then subsequently cleaned, dried, and stored under refrigeration. About 150 seeds from this hybrid population were then later planted at the property under the Inventor's control, and which is located in Roseville, Calif. This planting took place in the spring of 2011.

At the aforementioned Roseville, Calif. location, the respective seeds were germinated in small, individual containers where they were subsequently grown into small seedlings. By the Fall of 2011, a total of 98 seedlings were produced from this aforementioned seed population, and were then, subsequently, field planted in a row at a testing area near Traver, Calif., and which is located in Tulare County, in the San Joaquin Valley. The San Joaquin Valley is the principal fig growing area of California. The aforementioned 98 seedling population from which the 'S-64' fig tree selection was developed received alpha-numeric identification numbers 'S-1' through 'S-98', respectively. From among this family of young seedlings, the subject seedling tree which was identified and evaluated as 'S-64', was selected by the Inventor for further testing, and asexual reproduction. The new fig tree 'S-64' was first grafted, in 2014, by the Inventor into an existing fig tree which was approximately 5 years old. This new graft of the 'S-64' fig tree produced mature fruit which was then evaluated in August 2015. It is the inventor's considered opinion that this first asexual propagation produced fruit and vegetation that is identical in all respects to the originally discovered 'S-64' fig tree which was produced by the above-mentioned, controlled, cross-pollination.

SUMMARY OF THE VARIETY

The new fig tree variety 'S-64' produces a green to yellow skinned fig of the common or persistent type. The new variety of fig tree is medium in size, precocious, and is further considered productive, and a regular bearer of high quality figs. At the time of the present application, the new tree had not produced a first, or breba crop, but has produced an abundant second, or main crop having very desireable fruit. The fruit eye of the fruit which is produced by the newly discovered fig tree is small in size, and thereby inhibits insect, and other disease generating organism from gaining access into the fruit. The fruit skin, and the meat of the fruit is moderately thick and durable, thus making the fruit highly adaptable for packing and shipping in the fresh fruit market industry. Additionally, the fruit pulp has a very attractive strawberry-red color. Further, the fruit pulp is fine textured, and has an exceptionally rich flavor. The fruit produced by the new fig tree has an excellent size, and holds its size later into the season than many other commercial fig varieties thus extending the season for prime-sized and quality flavored figs.

BRIEF DESCRIPTION OF THE DRAWINGS

The accompanying drawings are color photographs of the present variety of fig tree.

The colors in the enclosed photographs are as nearly true as is reasonably possible in color photographs of this type. However, due to chemical development, processing, and printing, the leaves and fruit depicted in these photographs may or may not be accurate when compared with the actual botanical specimens. For this reason, future color references should be made to the color designations as found in The Royal Horticultural Society Colour Chart, 3$^{rd}$ Edition, and which was published in London, Great Britain, in 1995. Common color names are also occasionally used.

NOT A COMMERCIAL WARRANTY

The following detailed description has been prepared to solely comply with the provisions of 35 U.S.C. §112, and does not constitute a commercial warranty, [either expressed or implied], that the present variety will, in the future, display all the botanical, pomological, or other characteristics as set forth, hereinafter. Therefore, this disclosure may not be relied upon to support any future legal claims including, but not limited to, breach of warranty of merchantability, or fitness for any particular purpose, or non-infringement which is directed, in whole, or in part, to the present variety.

DETAILED DESCRIPTION

Referring more specifically to the pomological and botanical details of this new and distinct variety of fig tree, the following has been observed during the 2015 growing season under the ecological conditions prevailing in a testing area which is located near the town of Traver, in Tulare County, Calif. All major color code designations are made by reference to The Royal Horticulture Society Colour Charts, 3$^{rd}$ Edition, and which was published in London, Great Britain, in 1995.

TREE

Figure 1:
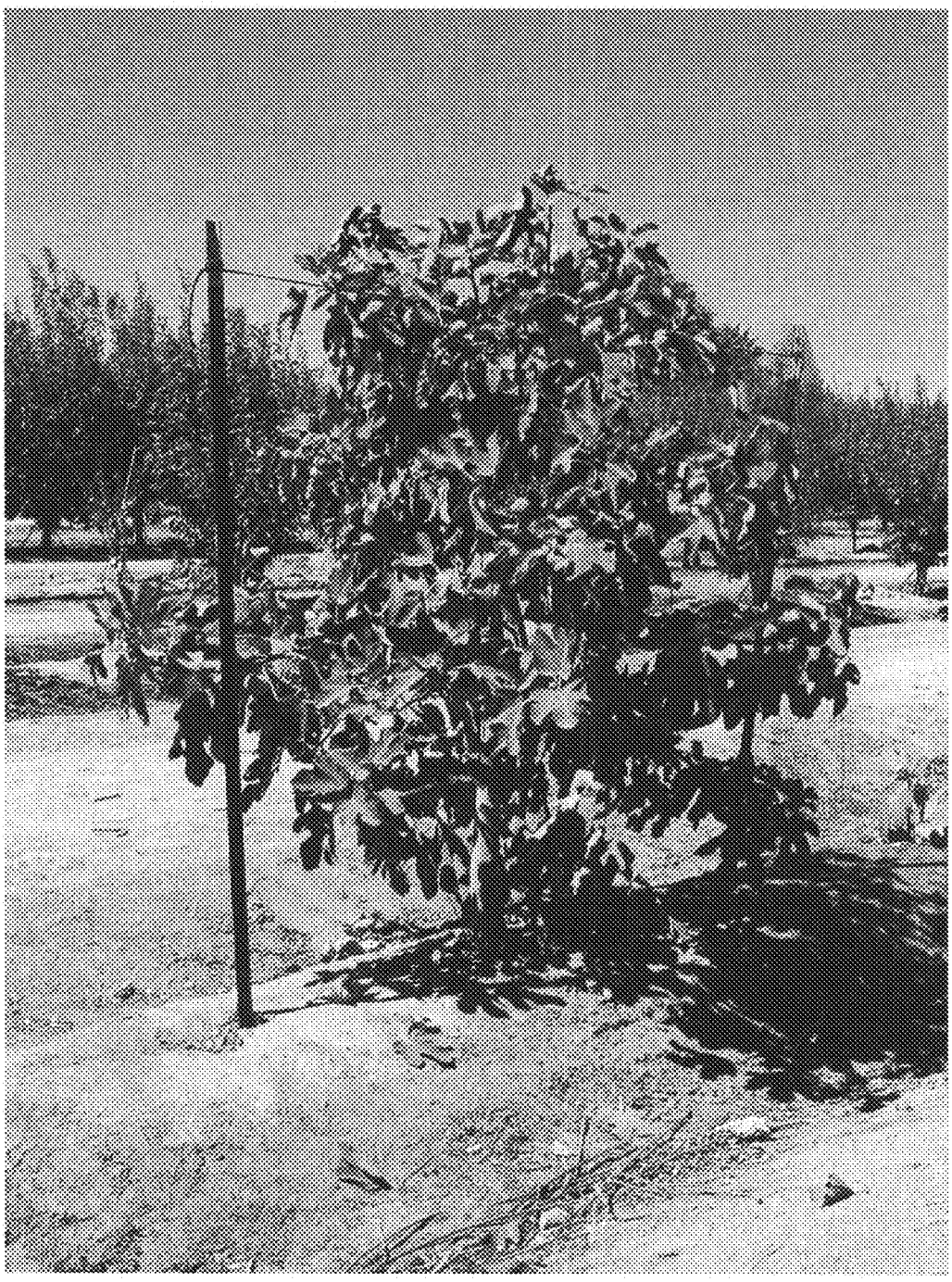
FIG. 1 is a photograph of the original fig tree 'S-64', and which is growing in the San Joaquin Valley of Central California.
Figure 2:
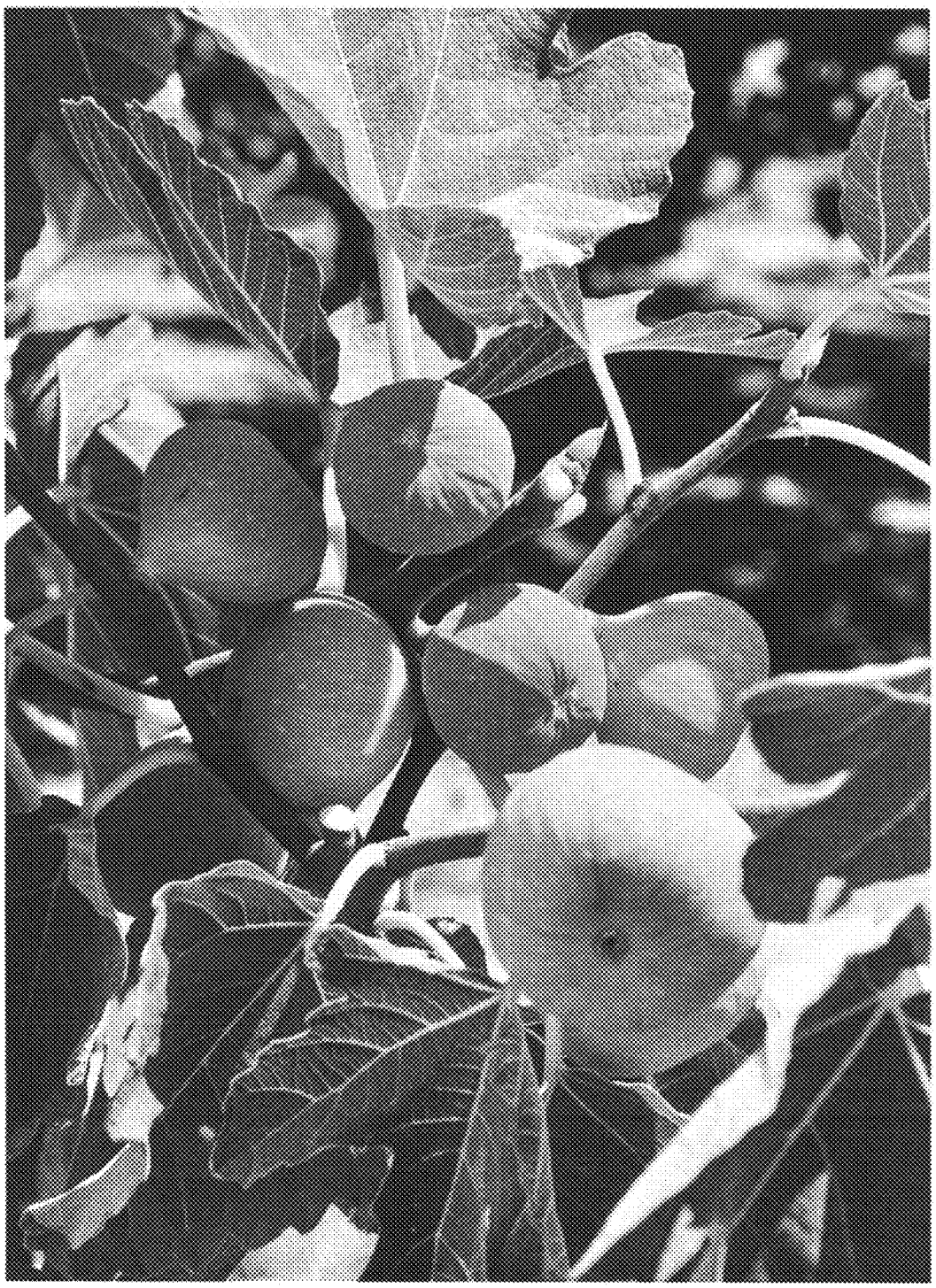
FIG. 2 shows the growth characteristic of the new fig tree displaying a second-crop of fruit on the original fig tree as seen in FIG. 1. Ripe fruit of the new variety of fig tree are seen in the foreground of this photograph.
Figure 3:
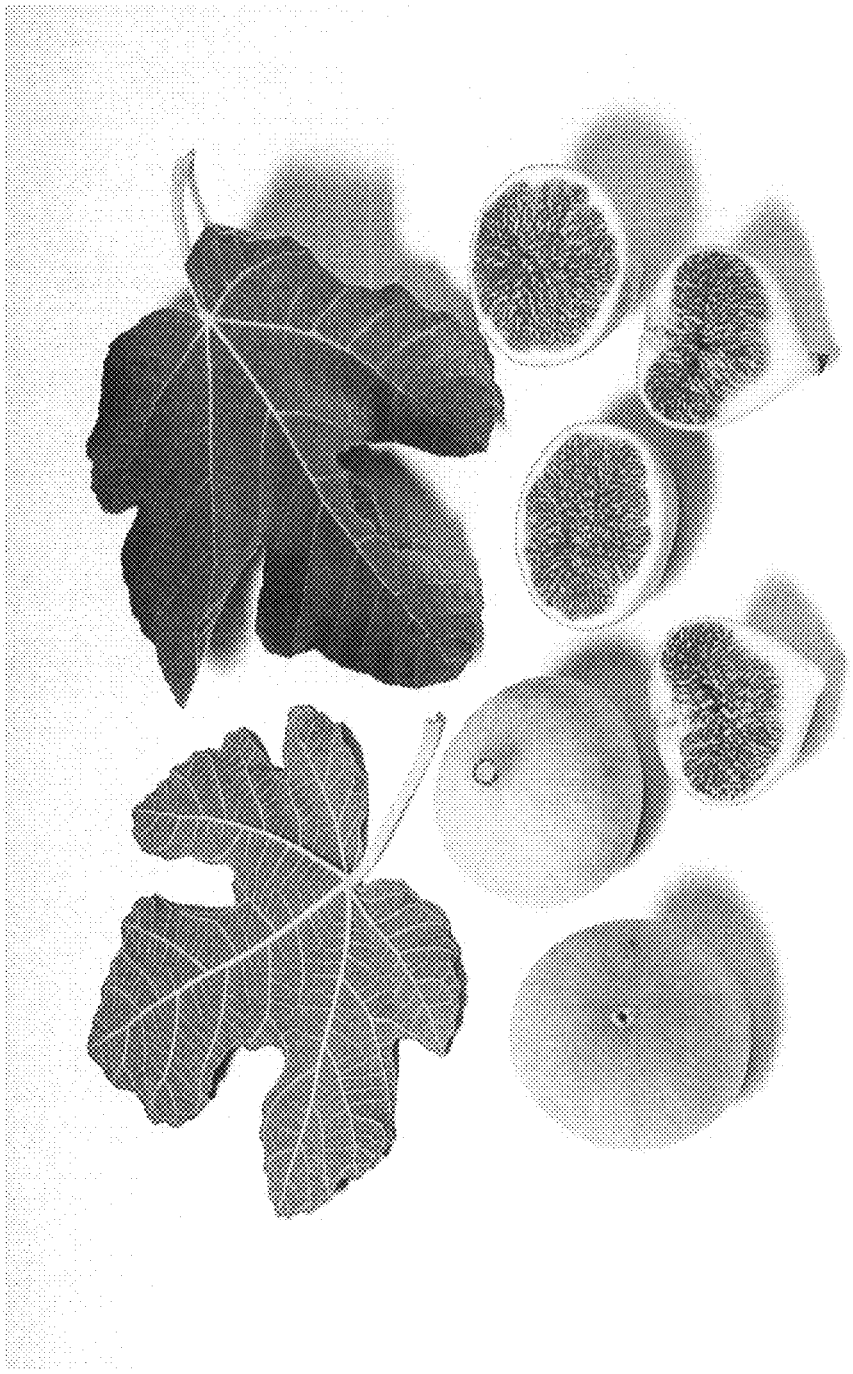
FIG. 3 shows several leaves produced by the present variety of fig tree, and which illustrate the dorsal and ventral coloration, and other characteristics thereof, and several mature fruit which are ripe for harvesting and shipment. Additionally, several other fruit have been cut in half so as to show the interior, pulp coloration, and other characteristics thereof.

Tree size: The tree as described hereinafter is the original tree derived from the aforementioned cross-pollination, and which took place in 2010. The seed which germinated, and produced the tree as seen in FIG. 1, was first planted in a container in 2011, and the resulting seedling tree was field planted in a testing area near Traver, Calif. in the fall of 2011. The tree as shown in the attached photograph (FIG. 1), is of medium size, and further had a total tree height, in 2015, of 7 feet. About 14 to about 24 inches of the tree as seen in FIG. 2 represented the current season's growth.

Tree width: Approximately 6 ft.

Tree spacing: Originally the trees were spaced about 3 feet apart down the row, and about 18 feet between the rows. Subsequently, the tree spacing within a row has been altered, and now more closely approximates about 6 feet between the adjacent trees.

Tree vigor: Considered hardy under typical San Joaquin Valley climatic conditions.

Tree form: Upright to upright-spreading.

Productivity: Considered precocious, and productive.

Fig type: Considered "common" or "persistent". As should be understood this type of fig tree does not need to be pollinated or "caprified" in order to set a mature fruit.

TRUNK; SCAFFOLDS; AND BRANCHES

Trunk size: About 10 cm. in diameter when measured at a distance of about 10 cm. from the top of the soil surface.

Trunk color: Variable, with several shades of gray being present, [Fan 4-Sheet 201 D], to a darker gray color, [Fan 4-Sheet 201 B].

Trunk surface texture: Considered slightly roughened, and appearing longitudinally striated, and having shallow furrows.

Lenticel form: The lenticels appear flattened, horizontally.

Lenticel width: About 2 to about 8 mm.

Lenticel height: About 1-2 mm.

Lenticel surface texture: Roughened, and further having a calloused surface.

Lenticel color: Brown [Fan 4-Sheet 177C].

Scafford numbers: Generally 3 main scaffords arise from the tree trunk.

Scafford diameter: About 27-31 mm. when measured basally.

Scafford surface texture:

*Generally*.—This surface texture appears less roughened than the trunk, although the surface texture is still somewhat longitudinally striated.

Scaffold lenticels:

*Generally*.—Present, and similar to the lenticels as seen on the tree trunk.

Scaffold color:

*Typically*.—Light Gray [Fan 4-Sheet 201D].

Secondary branches:

*Generally*.—These branches arise from the scaffolds discussed, above, and are variable in size.

Secondary branch diameters: The stronger, secondary branches are about 17 mm. in diameter when measured, basally.

Secondary branch color: Variable from a dark brown [Fan 4-Sheet 177B], to a still darker brown color, [Fan 4-Sheet 200C].

Lenticels:

*Generally*.—Numerous light colored lenticels are present, and have a color as seen in Fan 4-Sheet 165C.

Lenticel length: About 1-4 mm., and further appearing flattened longitudinally.

Secondary branch surface texture: Usually pubescent, and having numerous very short, and relatively stiff hairs scattered across the branch surface.

Internodes: The Internode length of the secondary branches vary considerably, from about 11 to about 21 mm., when measured near the shoot tips, to about 28 to 52 mm. when measured at mid-shoot.

Shoot tip bud color: Variable, from a light green-yellow, [Fan 3-Sheet 145C]; to a brighter yellow-green, [Fan 4-Sheet 160B].

Bud tip position: The angle of the bud tip is most frequently oblique to the plane of the shoot.

LEAVES

Leaf size:

*Generally*.—Considered large in size, and average in thickness. The following leaf measurements were taken from mature leaves growing at, or below, mid-shoot on vigorous, current season's growth.

Leaf width: Variable, from about 16 to about 20.5 cm.

Leaf length: About 14 to about 18.5 cm, not including the petiole.

Leaf thickness: Considered average for the species.

Leaf surface texture: Both the upper and lower leaf surfaces are pubescent. The leaf pubescence on the upper surface is short, stiff and prickly. The pubescence on the lower surface is also short, but substantially softer.

Leaf reflectance: The leaf surfaces appear relatively dull.

Leaf form: Somewhat variable. The leaves are typically palmately lobed. Typically 5 lobes are present.

Leaf lobe shape: Spatulate in form.

Leaf base form: Calcarate.

Leaf sinuses:

*Generally*.—Medium in depth. The sinus bottoms are "u-shaped" and often doubly so.

Leaf veins:

*Generally*.—Prominent on the lower leaf surface, and less so on the upper surface of the leaf. The leaf veins on both the upper and lower surfaces of the leaf are highly pubescent.

Leaf marginal shape: Generally crenate, with some variations. The crenations are low, and widely spaced. The outer leaf lobe margins are typically crenate, and the inner leaf lobe margins, within the leaf sinuses, are most frequently linear. The edges of the leaves are slightly undulate, and cupped inwards.

Leaf color: The upper leaf surface color is a dark green [Fan 3-Sheet 138A]. The surface color of the lower leaf surface is a lighter, green color [Fan 3-Sheet 138B].

Leaf vein color: Yellow-green [Fan 3-Sheet 145C].

Leaf vein surface texture: Highly pubescent.

Leaf petiole length: About 5.7 to about 8 cm.

Leaf petiole thickness: Variable, from about 5 to about 6 mm in diameter when measured, basally.

Leaf petiole color: A light green-yellow color, [Fan 3-Sheet 154D].

Leaf petiole surface texture: The surface texture of the petioles are covered with an abundance of a soft, fine, pubescence.

FIG TREE FLOWERS

Generally: The fig fruit includes a hollow receptacle identified, horticulturally, as the syconium. Many very small pedicelate flowers develop within this syconium, and are attached to the inner surface, thereof. These small flowers, which are nondistinctive, can be pollinated by the small fig wasp, *Blastophaga pesnes* L. As each fruit initiates growth in the leaf axills, and along the expanding shoot, and throughout a growing season, the fig wasp pollinates same. It should be understood that the tiny flowers become receptive when the syconium is about 1 to 2 cm in diameter. These florets have a 5-part perianth, and are unisexual, and have either a long-styled, or short-styled, pistillate flowers. As will be appreciated, 4 types of fig trees occur horticulturally. These include the caprifig fig tree which is a primitive-type of cultivated fig, and where the fig wasp accomplished its lifecycle. This is the only type of fig tree that sheds pollen, and is most frequently inedible. The 'Smyrna' type of fig tree is also known, and only matures fruit after pollination by the fig wasp. When pollinated, the presence of fertile embryos stimulates the fig fruit to remain on the tree and ripen. If this type of fig tree is not pollinated, the fruit will begin to grow, but then at about the size of an inch, or a little more in diameter, the fruit shrivels and falls off of the tree. A third, recognized fig tree variety is the "common" or "persistent" type of fig tree. The fruit produced by this type of fig tree does not need to be pollinated by the fig wasp in order for the fruit to remain on the tree, and come to full maturity. Finally, another variety of fig tree is the 'San Pedro' type of fig tree. This type of fig tree is an intermediate type, and where the first, or breba crop, is persistent, but the second, or main, crop is of the 'Smyrna' type, and further needs pollination to mature the crop. As earlier noted, the new fig tree variety 'S-64', is of the "common" or "persistent" type, and does not need to be pollinated to set, and mature a second, or main crop or fruit.

FRUIT

Generally: The description which follows was taken from a second or main crop which was produced by the new fig tree 'S-64'. As should be understood many fig trees produce 2 distinct crops. The first crop, which is typically referred to as the breba crop, is usually light in volume, and the fruit size is larger than that of the second crop.

This breba crop is borne on the previous season's shoots, and usually matures in early June under the ecological conditions prevailing in the San Joaquin Valley of central California. This maturity date is variable, from year-to-year. The second crop, which is often called the main crop, usually makes-up the bulk of the fig crop production for any particular growing season. The second crop fruit size is usually smaller, at least to some degree, relative to the fruit size of the breba crop, and further, the fruit matures later in the season than that of the breba fruit. The harvesting time for the second, or main crop usually begins about mid-July, and continues through August and September, and sometimes later, depending upon the environmental conditions prevailing in the San Joaquin Valley of Central California. The second, or main crop is borne on the axils of the current season's shoots. The second, or main crop harvesting finishes for the growing season when the current season's shoots terminate growth, and which is usually due to heat or drought conditions, or when climatic factors such as fog, rain, frost, etc. damages the fruit, and makes it unsaleable. The description which follows relates to the second, or main crop, and which further is produced by the new fig tree variety, 'S-64'. The present, new variety of fig tree has not, heretofore, produced a breba crop. This does not mean that the fig tree 'S-64' will never produce a breba crop. However, experience has shown me that young fig seedlings may take an extended period of time to begin producing a breba crop due to various juvenility factors, and then when the wood becomes more fully mature, breba fruit will begin to appear.

DESCRIPTION OF THE SECOND, MAIN CROP

The description as provided, hereinafter, was taken from a tree which is located in a testing area which is located near Traver, Calif. This tree is the original seedling tree of the 'S-64' fig tree selection, and is now 5 years old.

Crop size:

*Generally*.—Average for commercial fig tree varieties. The main crop was borne on the current season's growth.

Fruit maturity:

*Generally*.—Variable, and ranging from fully ripe, to small, green, and immature fruit. See FIG. 2.

Fig tree type: Common or persistent. The new tree does not need pollination [caprification] in order to set a mature fruit. The description which follows relates to fully mature fruit.

Fruit maturity, when described: Generally the fruit of the present variety was mature for harvesting on 15 Jul. 2015 under the ecological conditions prevailing near Traver, Calif. The 2015 growing season was approximately one (1) week or more, earlier, than average, for the central Valley of California.

Fruit production:

*Generally*.—The second or main crop of figs are successfully produced in the axils of current season's shoots from about mid-July, until later in the Fall. Commerical fig production terminates when the shoots stop elongating, and which is usually due to hot weather, or drought conditions, or further when other weather or ambient factors such as rain, frost, and the like, makes the fruit unsaleable.

Fruit size:

*Generally*.—Considered large.

Fruit production: Considered abundant.

Fruit length: Variable, from about 44 to about 67 mm.

Fruit width: Variable, from about 51 to 65 mm.

Fruit weight: Individual fruit can vary from about 54 grams, to as much as 107 grams. A very high percentage of the main crop exceeds 50 grams in weight.

Fruit form:

*Generally*.—Variable, in some instances the fruit is oblate in form, and has a neck. Occasionally the fruit may be spherical in form with a neck.

Fruit neck:

*Generally*.—The fruit neck is variable in length from very short to medium.

Fruit neck length: About 2 mm to about 18 mm, in length.

Fruit neck color: Variable, Green [Fan 3-Sheet 145A], to a more yellow-green [Fan 3-Sheet 151D].

Fruit stem length and diameter: Short, and relatively thick, about 3.0 to about 6.0 mm., in length, and about 6.0 mm. in diameter.

Fruit stem color: Variable, from green [Fan 3-Sheet 149B] to a greenish yellow [Fan 3-Sheet 151C].

Fruit stem surface texture: Pubescent. The pubescence is very fine and short.

Bracts:

*Generally*.—Several irregular shaped bracts are present at the apex of the stem, and where the stem is attached to the fruit neck. The bracts form an irregular ring around the stem apex.

Bract color: Light-green [Fan 3-Sheet 151D].

Fruit ribs:

*Generally*.—Longitudinal ribbing is present on the surface of the fruit. As a general matter, the ribs are continuous, and extend from the fruit eye to the fruit base. The fruit ribs taper at both the eye, and the stem ends. The ribs are only slightly raised.

Rib color: Typically darker than the surrounding skin surface color, and variable from a dark green [Fan 3-Sheet 144C], to a lighter, yellow-green [Fan 3-Sheet 151D].

Fruit eye:

*Generally*.—Small and relatively tight.

Eye diameter: About 1 to about 3 mm.

External scales: Present, and surrounding the eye. The external scales are further considered small, and are about 1 to 2 mm., in length.

External scale color: A pale yellow-green [Fan 3-Sheet 154D], or at times they appear lighter in color, and nearly white. The scales surrounding the fruit are generally appressed relative to the fruit body. The external scales overlap, and extend from the eye perimeter down into the ostiole of the fruit. The external scales darken, somewhat, with increasing maturity, and pinkish colored flecking can, at times, appear on the external scale surfaces.

External scale form: Roughly conic, with some variation.

Fruit skin:

*Generally*.—Medium, to relatively thick, and considered durable.

Fruit skin surface texture: Slightly pubescent, with very short, and fine hairs being present.

Fruit skin appearance: Only very slightly glossy. A thin, waxy bloom is present over the entire skin surface. Almost no skin checking is present on the fruit. Further, the skin peels easily from commercially ripe fruit.

Skin flecking:

*Generally*.—Numerous white colored skin flecks are seen on the fruit skin, [Fan 4-Sheet 155C]. The skin flecking primarily occurs laterally on the skin surfaces.

Skin fleck shape: Oval and having a width of about 1 to 2 mm, and a vertical height of about 2 to about 4 mm.

Skin color: Variable, from a light yellow-green at commercial maturity, [Fan 3-Sheet 145A], to a lighter, yellow-green which occurs with advancing maturity [Fan 3-Sheet 151B]. The darker, yellow-green color can persist at maturity, and encircles the fig fruit eye area.

Fig meat color: The fig meat appears white at a location which is just under the skin, [Fan 4-Sheet 155A].

Fig meat thickness: Variable, from about 3, to about 3.5 mm., in thickness, when measured laterally, but it is still thicker near the fruit stem area. This thickness is about 5 to about 7 mm.

Fig meat texture: Moderately firm, and sweet.

Fig pulp color: A very attractive, deep, bright, strawberry-red [Fan 4-Sheet 180A]. The fig syconium is well-filled, and there is only a little air space in the central area of the fruit where the pulp surfaces meet.

Fig pulp texture: Uniform, and finely grained.

Seeds:

*Generally*.—An abundant number of small seeds are present in the fig pulp. In this regard, the seeds that are unpollinated cenocarps are hollow, and have no internal embryo.

Seed shape: Variable, from oval to occasionally ovate.

Seed size: About 1 mm in diameter.

Seed color: Tan [Fan 4-Sheet 165C].

Fig flavor: Considered very good for the species. It is both sweet and rich and resembles the taste of the very high quality fruit produced by the 'Calimyrna' fig tree.

Fruit usage: The fruit of the fig tree 'S-64' is primarily suited for the fresh market. Its potential use for the dry market has not been explored.

VARIETAL COMPARISONS

In comparison to the 'Desert King' fig tree, which is the female parent of the new variety of fig tree, the 'Desert King' fig tree produces fruit having a similar, greenish-yellow skin color, but each have other distinct differences. For example, the 'Desert King' fig tree produces fruit having a moderately open eye, whereas, the eye as observed on the fruit produced by the 'S-64' fig tree is small, and tight. Further, the 'Desert King' fig tree is a 'San Pedro' type fig tree where the first, or breba crop sets without pollination, but the second, or main, crop, needs to be pollinated by the fig wasp in order to set, and mature fruit. In contrast, the fruit produced by the 'S-64' fig tree is of the persistent or "common" type, and does not need to be pollinated in order to set, and mature fruit. In addition to the foregoing, the pulp color of the fruit produced by the 'Desert King' fig tree can be variable from an amber, to a medium-red. However, the pulp color of the fruit produced by the 'S-64' fig tree is uniformly, a deep, bright, strawberry red color which becomes darker with advancing maturity.

In comparision with the fig tree variety 'Calimyrna', it should be understood that the 'Calimyrna' fig tree makes up almost half of the genome as found in the caprifig tree '91C', and which is the male [pollen] parent of the new fig tree 'S-64'. It should be appreciated that the 'Calimyna' fig tree is widely grown in the state of California, and further produces fruit which are useful for both the fresh, and dry markets. The 'Calimyrna' fig tree, in the past, has been generally considered as producing the best flavored figs that are available in commerce. Both the 'Calimyrna' fig tree, and the fruit produced by the 'S-64' fig tree both have large sized greenish-yellow skinned fruit which have excellent quality. However, the fruit produced by the 'Calimyrna' fig tree has a very large fruit eye that allows an entry point into the center of the fruit for insects and other undesirable organisms. In contrast, the eye of the fruit as produced by the 'S-64' fig tree is small, and tight, and which restricts entry of insects and disease causing organisms into the fruit. Additionally, it should be noted that the 'Calimyrna' fig tree is a "Smyrna" type fig tree, that is, it requires pollination by the fig wasp in order to set, and mature fruit. In contrast, the fruit produced by the 'S-64' fig tree does not require any pollination by the fig wasp to set, and mature fruit. Lastly, the fruit produced by the 'Calimyrna' fig tree has an amber-colored fruit pulp, while the pulp color of the fruit produced by the 'S-64' fig tree is a deep, bright, strawberry-red.

Although the new variety of fig tree possesses the described characteristics when grown under the ecological conditions prevailing in the San Joaquin Valley of central California, it should be understood that variations of the usual magnitude and characteristics incident to changes in growing conditions, fertilization, pruning, and pest control, as well as horticultural management practices, are to be expected.

Having thus described and illustrated my new variety of fig tree, what I claim is new, and desire to secure by Plant Letters Patent is:

1. A new and distinct variety of fig tree, as substantially shown and described, and which is characterized principally as to novelty by bearing fruit which has excellent size and holds its size later into the season than other commercial fig varieties thus extending the season for prime-sized and quality fresh figs under the ecological conditions prevailing in the San Joaquin Valley of Central California.

* * * * *